United States Patent [19]

Haber et al.

[11] Patent Number: 5,490,736
[45] Date of Patent: Feb. 13, 1996

[54] STYLUS APPLICATOR FOR A REHYDRATED MULTI-CONSTITUENT MEDICATION

[75] Inventors: Terry M. Haber, El Toro; William H. Smedley, Lake Elsinore; Clark B. Foster, Laguna Niguel, all of Calif.

[73] Assignee: Habley Medical Technology Corporation, Laguna Hills, Calif.

[21] Appl. No.: 302,586

[22] Filed: Sep. 8, 1994

[51] Int. Cl.$^6$ .......................... A61M 35/00; A47L 13/17
[52] U.S. Cl. .............. 401/40; 401/41; 401/132; 401/196; 604/2; 604/3
[58] Field of Search .............. 401/40, 41, 132, 401/196; 604/2, 3

[56] References Cited

U.S. PATENT DOCUMENTS

| | | | |
|---|---|---|---|
| 1,293,401 | 2/1919 | Gibson | 604/3 |
| 1,607,768 | 11/1926 | Meusel | 401/132 X |
| 3,349,966 | 10/1967 | Schwartzman | 401/41 X |
| 3,519,364 | 7/1970 | Truhan | 604/2 X |
| 3,759,259 | 9/1973 | Truhan | 604/3 |
| 5,054,948 | 10/1991 | Honda et al. | 401/196 |
| 5,180,244 | 1/1993 | Hirose | 401/132 X |

FOREIGN PATENT DOCUMENTS

| | | | |
|---|---|---|---|
| 607405 | 7/1926 | France | 401/41 |
| 302887 | 1/1955 | Switzerland | 401/41 |

*Primary Examiner*—Steven A. Bratlie
*Attorney, Agent, or Firm*—Hawes & Fischer

[57] ABSTRACT

A compact, single-use stylus applicator is disclosed having a dry medication (e.g. a dehydrated topical astringent disinfectant that is adapted to treat acne and has been reduced to crystalline form by lyophilization) stored in a first chamber. A liquid diluent is stored in a second chamber. Fluid communication between the first and second chambers is blocked by a barrier. By compressing the second chamber, a corresponding hydraulic pressure is generated in the diluent which defeats the fluid blocking integrity of the barrier. Accordingly, the diluent in the second chamber is introduced under pressure to the dry medication in the first chamber to rehydrate and activate the acne medication. The reconstituted multi-constituent liquid medication is absorbed by a stylus-shaped swab so as to be applied directly to a tissue area as a topical treatment for acne or other skin disorders.

11 Claims, 6 Drawing Sheets

STYLUS APPLICATOR FOR A REHYDRATED MULTI-CONSTITUENT MEDICATION

BACKGROUND OF THE INVENTION

1. Field of the Invention

This invention relates to a compact, single use stylus applicator in which a lyophilized medication is packaged in a wafer or powder form to be rehydrated prior to use by a liquid diluent so that a precise amount of the reconstituted medication can be applied directly to a target site for the treatment of acne, and the like.

2. Background Art

It is sometimes desirable for those suffering from acne or other skin disorders to periodically apply a topical medication to a tissue area to enhance treatment and speed healing. It is common to package the topical acne medication as a liquid or cream in a bottle or tube or as a series of moist pads in a jar. Because the liquid, cream and moisture is subject to evaporation with time, the shelf life of the usual packaged medication may be undesirably shortened. Moreover, once the container is opened and the medication is exposed to the atmosphere, some of the moist treatment pads may dry out while some of the liquid or cream medication may be lost or spilled.

In addition, it may not be convenient to carry on one's person a relatively large container in which the liquid medication or moist pads are packaged. More particularly, the user may have to transport a bottle, tube or jar even though only a small portion of the medication therein will be used during any given treatment. In this same regard, there is no readily available way for the user to control the application of a precise amount of acne medication to this tissue. Too much or too little liquid or cream is often dispensed from a bottle or tube. If the tissue area to be treated is small, the moist pad is known to have an excess of medication than that actually needed to adequately treat the acne.

The foregoing results in inefficiency and/or waste which can prove to be inconvenient, particularly if the medication is expensive or the acne requires a long period of treatment. In some cases, the user may have to replace the medication prematurely, because of the evaporation or inefficient use thereof. In other cases, the user may elect to forego treatment altogether, especially when travelling far from home.

SUMMARY OF THE INVENTION

In general terms, a compact single use stylus applicator is disclosed in which a multi-constituent medication is packaged and ready to be activated for direct application to a target site. According to a first embodiment of the invention, the applicator includes a hollow tubular proximal body and an opposing hollow tubular distal cap, each having an open end and a closed end and each manufactured from a gas and liquid impermeable, heat sealable material. A stylus-shaped absorbent swab projects outwardly from the open end of the proximal body. Located proximally of the absorbent swab is a medication wafer (or powder). The medication wafer is preferably a dehydrated topical astringent disinfectant that is known to treat acne and that has been reduced to crystalline form by a conventional lyophilization process. As an alternate embodiment, the medication wafer is replaced by an elongated medication plug that is sized to fit within a longitudinal compartment extending through the stylus-shaped absorbent swab. Located proximally of the medication wafer and extending laterally across the proximal body is a deformable elastomeric septum. A liquid diluent (e.g. a saline solution) is stored in the proximal body and separated from the dry medication wafer by the septum. In the packaged, ready-to-activate configuration of the applicator, the proximal body and distal cap are press fit together with the distal cap surrounding the swab projecting from the proximal body.

To activate and use the stylus applicator of the first embodiment, the distal cap is first pulled off the proximal body to expose the stylus-shaped swab. Next, the user squeezes the proximal body to generate a corresponding hydraulic force within the diluent to push the septum out of alignment across the proximal body and thereby open a fluid path between the diluent and medication wafer. Thus, the diluent is introduced to and mixed with the dry astringent disinfectant of the medication wafer. The medication is rehydrated to liquid form and absorbed through the swab by capillary action. Finally, the user moves the saturated swab into contact with the acne to be treated so that the liquid medication can be applied directly to the target site. When the topical treatment has been completed, the applicator is simply discarded.

According to a second embodiment of the invention, the applicator is formed from a single tubular hollow body manufactured from a gas and liquid impermeable, heat sealable material having its opposite ends sealed. A stylus-shaped absorbent swab is located within the sealed body. Also located within the body proximally of the absorbent swab is a medication wafer (or powder). The medication wafer is preferbly a dehydrated topical astringent disinfectant that is known to treat acne and that has been reduced to crystalline form by a conventional lyophilization process. Located proximally of the medication wafer and extending laterally across the applicator body is a barrier. The barrier is integrally formed with and fixedly attached across the body. A liquid diluent is stored at the proximal end of the body and separated from the dry medication wafer by the barrier. However, the barrier is provided with a series of score lines that are adapted to be ruptured to permit the integrity of the barrier to be defeated to place the diluent and medication wafer in fluid communication with one another. An area of the applicator body in which the absorbent swab is located is surrounded by a peripheral (e.g. notched) tear line which allows the applicator body to be severed.

To activate and use the stylus applicator of the second embodiment, the proximal end of the body is first squeezed so as to generate a corresponding hydraulic force within the diluent. The hydraulic force fractures the barrier along the score lines so that the fluid blocking integrity of the barrier will be defeated. The user continues to compress the proximal end of the body so that the liquid diluent is introduced to the dry medication wafer. Thus, the diluent is mixed with the astringent disinfectant of the medication wafer. The medication is rehydrated to liquid form and absorbed through the swab by capillary action. Next, the user holds the proximal end of the applicator body in one hand and with the other hand applies twisting and pulling forces to the opposite distal end. Accordingly, the applicator body will fracture along the preformed peripheral tear line so that the distal end of the body can be pulled off the proximal end to expose the stylus-shaped swab. Finally, the user moves the saturated swab into contact with the acne to be treated so that the liquid medication can be applied directly to the target site. When the topical treatment has been completed, the applicator is simply discarded.

DETAILED DESCRIPTION

Figure 1:
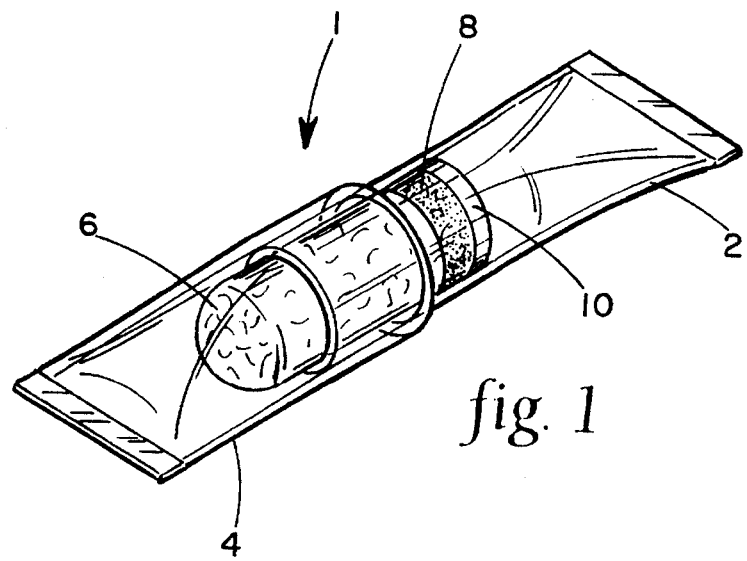
FIG. 1 is a perspective view of a compact, single use stylus applicator according to a first embodiment of the present invention in the packaged, ready-to-activate configuration.
Figure 2:
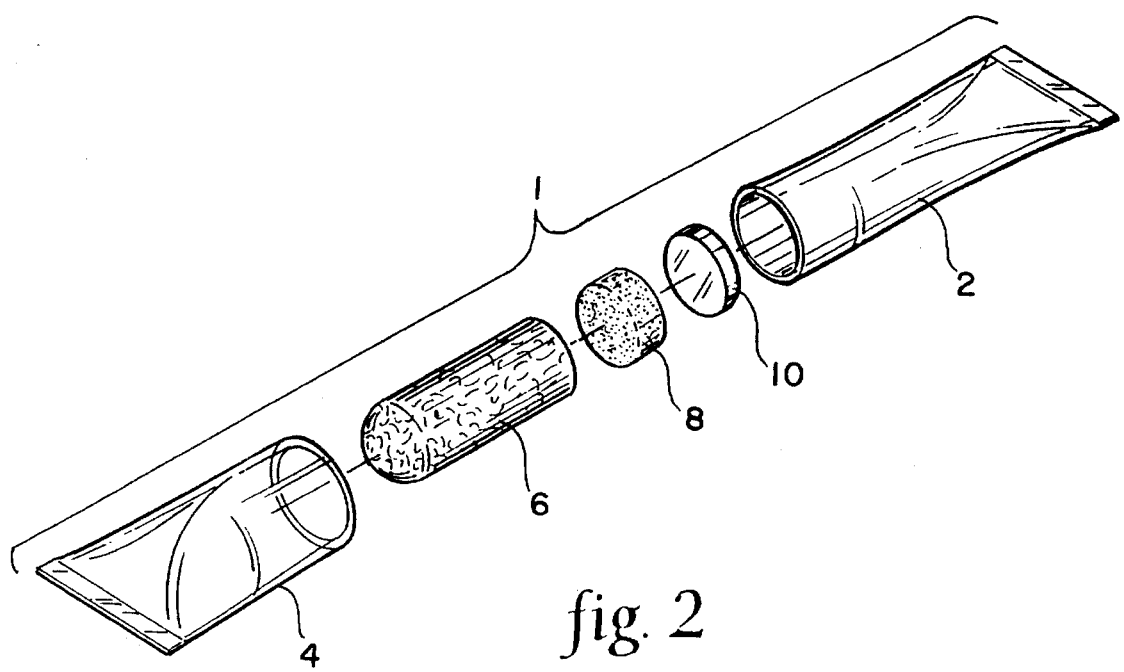
FIG. 2 is an exploded view of the stylus applicator of FIG. 1.
Figure 3:
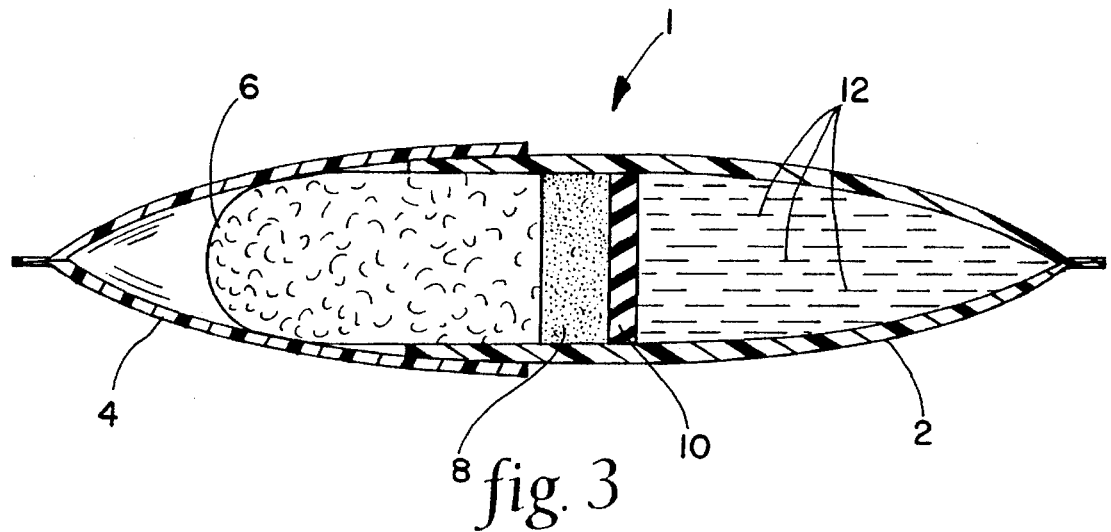
FIG. 3 is a cross-section of the stylus applicator of FIG. 1.

FIGS. 1—3A of the drawings illustrate a first embodiment of a compact, single use stylus applicator in which a topical acne medication is packaged and from which the medication can be applied directly to a target site for the treatment of acne. Referring initially to FIGS. 1, 2 and 3, an applicator 1 is shown for dispensing a precise amount of acne medication to a relatively small area. The applicator 1 includes a hollow tubular proximal body 2 and an opposing hollow tubular distal cap 4. The proximal body 2 and distal cap 4 are manufactured from a gas and liquid impermeable, heat sealable material that is suitable for thermal bonding. In this regard, one end of each of the proximal body 2 and the distal cap 4 is pinched and sealed, and the opposite end of each is open. By way of example only, a heat sealable material which may be used to manufacture the proximal body 2 and distal cap 4 is a commercially available Mylar/polyethylene barrier layer material.

Retained within the proximal body 2 of applicator 1 is a stylus-shaped absorbent (e.g. cotton or an open cell foam material) swab 6. Located proximally of absorbent swab 6 is a medication wafer 8. In accordance with the present invention, the medication wafer 8 is preferably a dehydrated topical astringent disinfectant that is known to treat acne and has been reduced to crystalline form by a conventional lyophilization process. However, the dehydrated disinfectant could also take the form of a powder. Located proximally of the medication wafer 8 is a deformable elastomeric (e.g. rubber) septum 10.

In the packaged, ready-to-activate configuration of the stylus applicator 1 shown in FIG. 3, a liquid diluent 12 is stored in the proximal body 2. As will be disclosed when referring to FIG. 3A hereinafter, the diluent (e.g. a saline solution) will be introduced to the dehydrated astringent disinfectant of medication wafer 8 to rehydrate and activate the acne medication. The septum 10 is located so as to extend laterally across the proximal body 2 to function as a barrier and thereby prevent the premature introduction of the diluent 12 to the medication wafer 8. However, and as will also be disclosed, the alignment of the septum 10 with the proximal body 2 of applicator 1 can be skewed under pressure to permit the diluent 12 to be released from proximal body 2.

Received within and projecting outwardly from the open end of the tubular proximal body 2 is the absorbent swab 6. In the packaged configuration of the applicator 1 shown in FIG. 1, the swab 6 projecting from the proximal body 2 is moved through the open end of the tubular distal cap 4. The proximal body 2 and the distal cap 4 are dimensioned relative to one another so as to be press fit together to establish an air-tight seal around the interface therebetween with the distal cap 4 surrounding the swab 6 projecting from the proximal body 2 (best shown in FIG. 3). The applicator 1 is now ready to be stored, transported and ultimately used so that the acne medication can be easily and accurately applied to a target site.

Figure 3A:
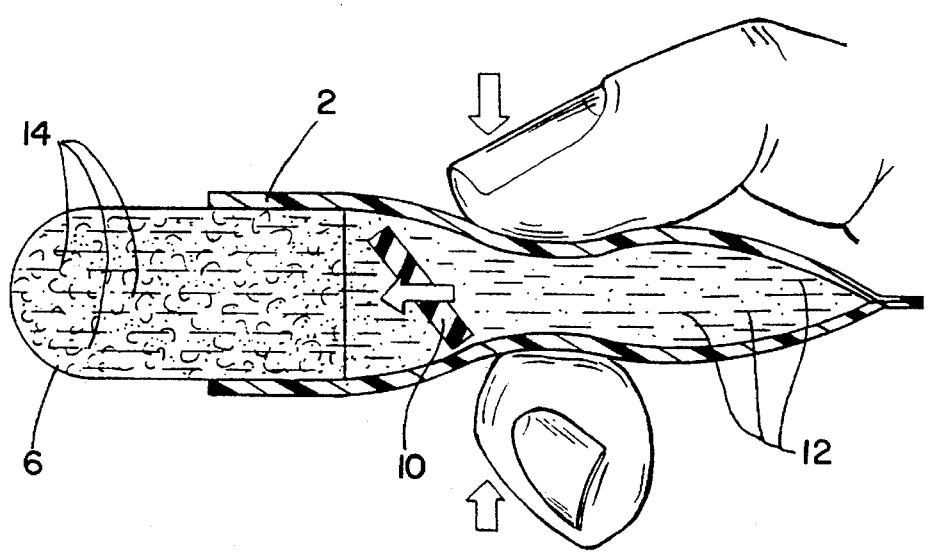
FIG. 3A is illustrative of the steps by which to activate and use the stylus applicator of FIG. 1.

The activation and use of the stylus applicator 1 to apply a topical acne medication to a target site is now disclosed while referring to FIG. 3A of the drawings. First, the user pulls the distal cap 4 off and away from the proximal body 2, whereby to expose the stylus-shaped absorbent swab 6 projecting from proximal body 2. Next, the user squeezes the proximal body (e.g. between his thumb and forefinger, as illustrated) so as to apply opposing compressive forces thereagainst in the direction of the reference arrows. The compressive forces applied to proximal body 2 create a corresponding hydraulic pressure within the diluent 12. The user compresses the proximal body 2 until the hydraulic pressure is sufficient to push the septum 10 out of its packaged alignment across the proximal body 2 to thereby remove the barrier between the diluent 12 and the medication wafer 8 (of FIG. 3).

With the septum 10 displaced relative to proximal body 2, the liquid diluent 12 is introduced, under pressure, to the medication wafer 8. Accordingly, the dry astringent disinfectant of wafer 8 is now mixed with the diluent and rehydrated to a liquid medication 14 which is absorbed through the swab 6 by means of capillary action. Finally, the user moves the saturated swab 14 into contact with the acne to be treated. By once against squeezing the proximal body 2, the hydraulic force generated within the diluent will be transferred to the swab 6 to cause the liquid acne medication 14 absorbed thereby to be dispensed directly to the target site. When the topical treatment has been completed, the spent applicator is simply discarded.

Figure 4:
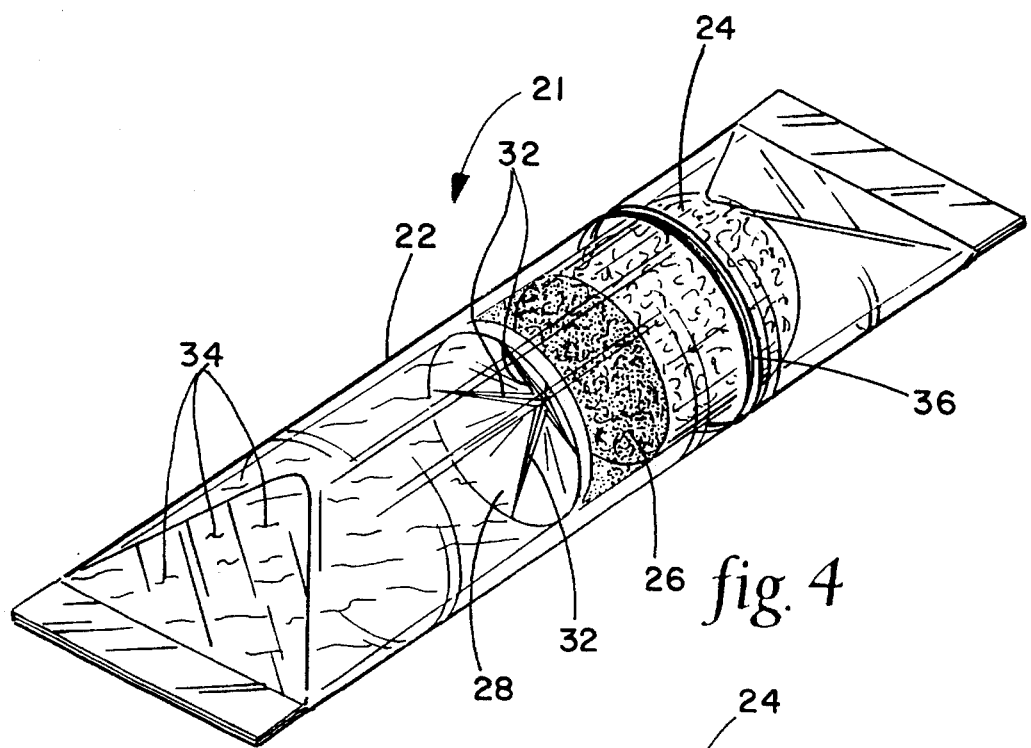
FIG. 4 is a perspective view of a compact, single use stylus applicator according to a second embodiment of the invention in the packaged, ready-to-activate configuration.
Figure 5:
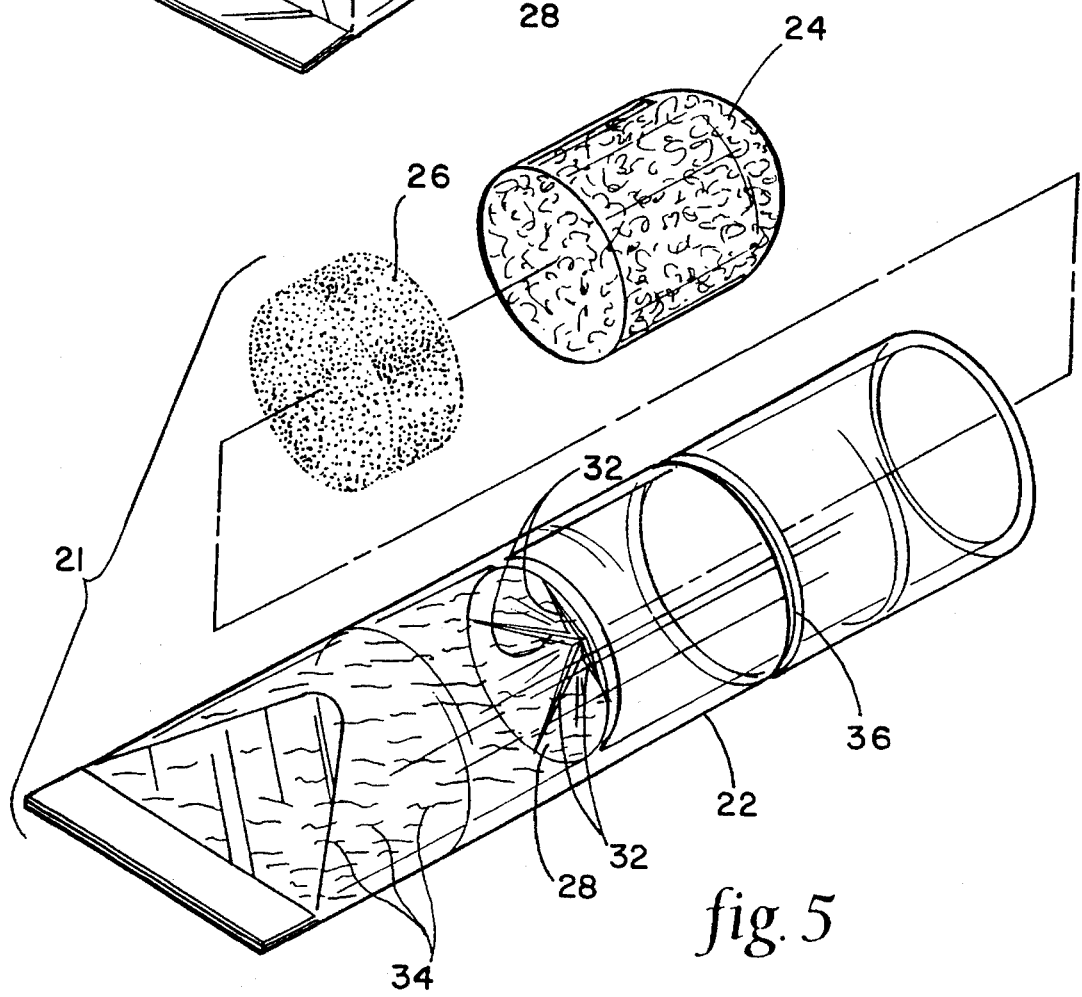
FIG. 5 is an exploded view of the stylus applicator of FIG. 4.
Figure 6:
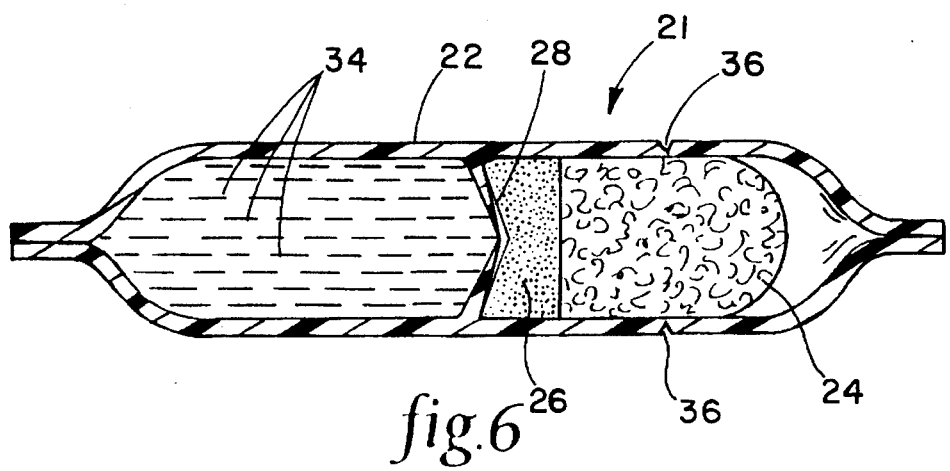
FIG. 6 is a cross-section of the stylus applicator of FIG. 4.

FIGS. 4—7B of the drawings illustrate a second embodiment for a compact, single use stylus applicator in which a topical acne medication is packaged and from which the medication is applied directly to a target site. Referring initially to FIGS. 4, 5 and 6, another applicator 21 is shown for applying a precise amount of medication to a relatively small area requiring treatment. Unlike the applicator 1 of FIGS. 1–3, the applicator 21 is formed from a single hollow tubular body 22. The tubular body 22 is formed from a gas and liquid impermeable, heat sealable material, and each end thereof is pinched and sealed.

Retained within the body 22 of applicator 21 near the distal end thereof is a stylus-shaped absorbent swab 24. Located proximally of absorbent swab 24 is a medication wafer 26. Like the medication wafer 8 of FIGS. 1–3, the medication wafer 26 is preferably a dehydrated astringent disinfectant that has been reduced to crystalline form by lyophilization. Located proximally of the medication wafer 26 and extending laterally across the applicator body 22 is a barrier 28. Unlike the septum 10 of FIGS. 1–3 which is displaced or misaligned relative to the applicator body, the barrier 28 is integrally formed with and fixedly attached across the applicator body 22 so as to isolate the proximal and distal ends of the applicator 21 from fluid communication with one another. However, barrier 28 is provided with a series of score lines 32 that, as will be disclosed when referring to FIG. 7A hereinafter, are adapted to permit the integrity of the barrier 28 to be defeated and the proximal and distal ends of the applicator 21 to lie in fluid communication with one another.

In the packaged, ready-to-activate configuration of the stylus applicator 21 shown in FIG,. 6, a liquid diluent 34 is stored at the proximal end of the applicator. With the barrier 28 relaxed and extending across the applicator 21, the introduction of the diluent 34 at the proximal end of the applicator to the medication wafer 26 at the distal end of the applicator is reliably blocked. As is also best shown in FIG. 6, the distal end of the applicator 21 is surrounded by a peripheral (e.g. notched) tear line 36 which allows the applicator body 22 to be severed.

Figure 7A:
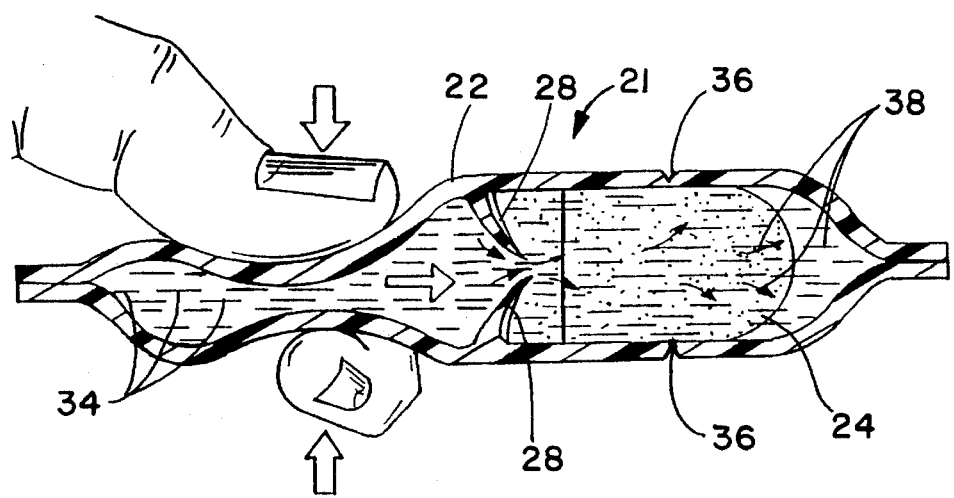
FIGS. 7A and 7B are illustrative of the steps by which to activate and use the stylus applicator of FIG. 4.

The activation and use of the stylus applicator 21 to apply a topical acne medication to a target site is now disclosed while referring to FIG. 7A of the drawings. First, with the applicator body 22 in tact, the user squeezes the proximal end of the applicator 21 (e.g. between his thumb and forefinger, as illustrated) so as to apply opposing compressive forces thereagainst in the direction of the reference arrows. The compressive forces applied to the proximal end of applicator 21 generate a corresponding hydraulic pressure within the diluent 34. The aforementioned compressive forces are applied until the hydraulic pressure of the diluent is sufficient to fracture the barrier 28 along the score lines 32 (of FIGS. 4 and 5). With the fluid blocking integrity of the barrier now defeated, the user continues to compress the proximal end of applicator 21 whereby to introduce the liquid diluent at the proximal end of applicator 21 to the medication wafer 28 near the distal end. As in the applicator 1 of FIG. 3A, the solid astringent disinfectant of wafer 26 is mixed with the diluent and rehydrated to a liquid medication 38 which is absorbed throughout the swab 24 by means of capillary action.

Figure 7B:
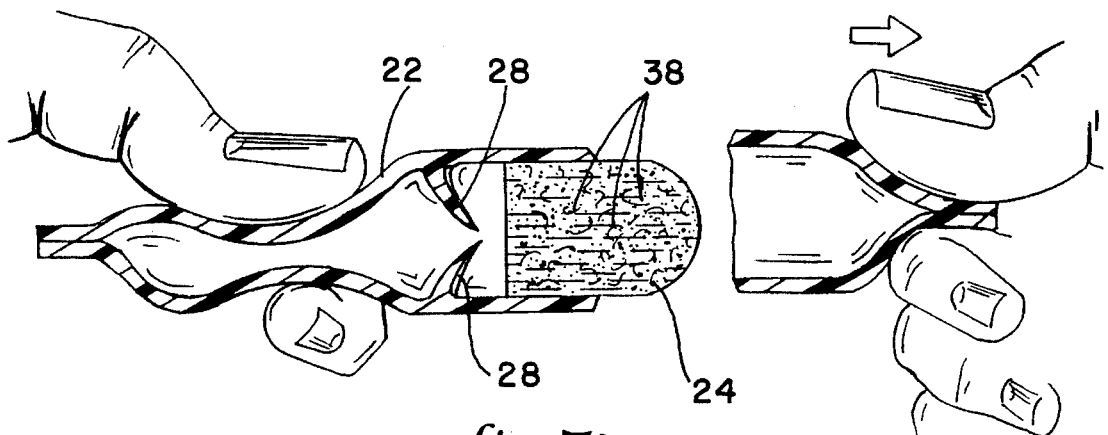

Next, and referring now to FIG. 7B, while holding the proximal end of applicator 21 in one hand, the user grasps the distal end with the other hand and applies twisting and pulling forces thereto. Accordingly, the body 22 of applicator 21 will fracture along the preformed peripheral tear line 36 (of FIG. 7A). When the distal end of applicator 21 is pulled off and away from the body 22, the swab 24 which has absorbed the liquid medication 38 will now be exposed and accessible to the user. Finally, the user moves the swab 24 into contact with the acne to be treated so that the liquid acne medication 38 can be applied directly to the target site. When the topical treatment has been completed, the spent applicator 21 is simply discarded.

It may be appreciated that by making the stylus applicator 21 with a one-piece body 22 (instead of separate proximal and distal body ends 2 and 4 as in the applicator 1 of FIGS. 1–3) and with an integrally formed barrier 28 (instead of a separate septum 10 as in the applicator 1), the number of parts necessary to manufacture the applicator 21 is less than the number of parts necessary to manufacture applicator 1. Therefore, and depending upon the manufacturing process employed, a lower number of component parts may contribute to a correspondingly lower manufacturing cost and/or ease of assembly.

Figure 8:
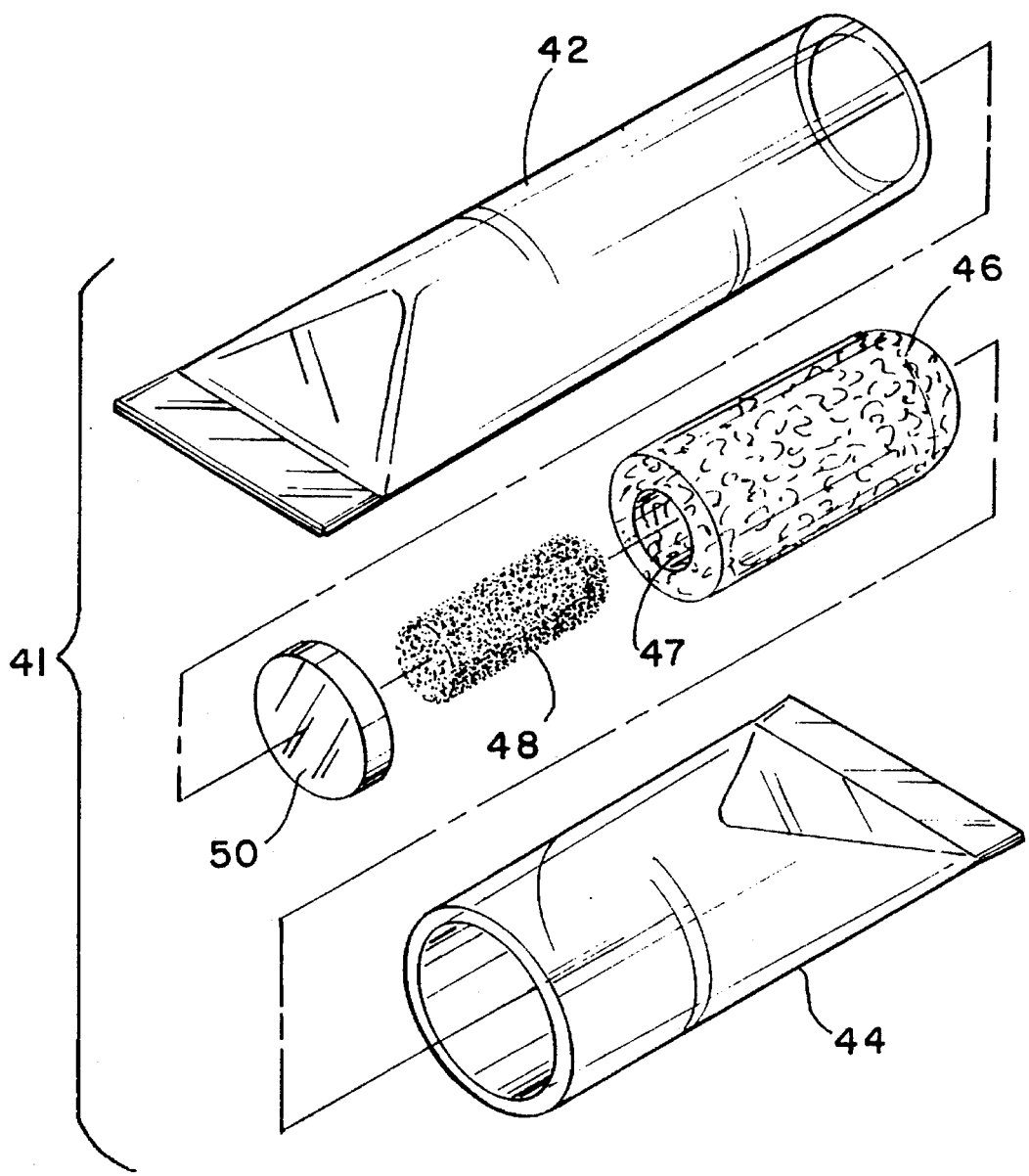
FIG. 8 is an exploded view of a compact, single use stylus applicator showing a modification to the stylus applicator illustrated in FIGS. 1—3A.
Figure 9:
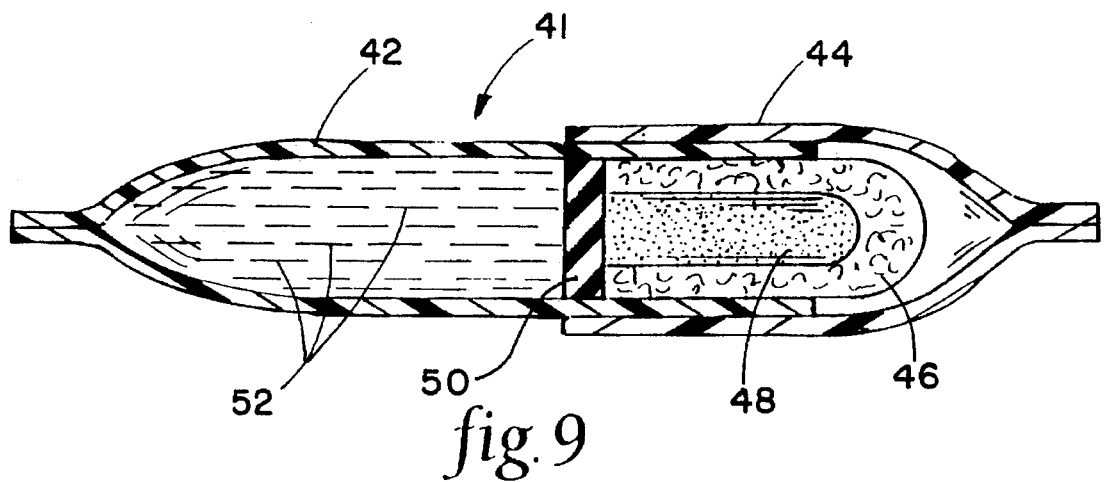
FIG. 9 is a cross-section of the stylus applicator of FIG. 8 in the packaged, ready-to-activate configuration.
Figure 9A:
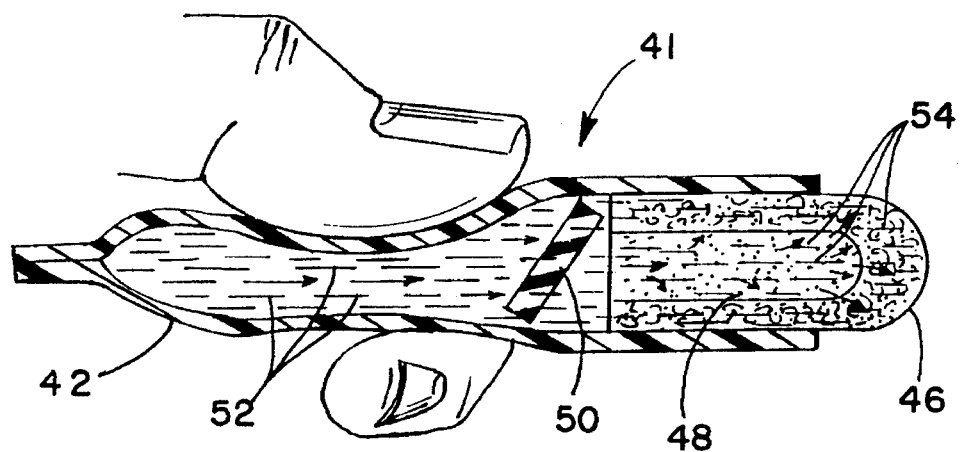
FIG. 9A is illustrative of the steps by which to activate and use the stylus applicator of FIG. 8.

FIGS. 8–9A of the drawings illustrate a modification to the previously disclosed compact, single use stylus applicator 1 of FIGS. 1–3. Referring initially to FIGS. 8 and 9, and as described with regard to the applicator 1, an applicator 41 is shown including a hollow, tubular proximal body 42 and an opposing hollow tubular distal cap 44, each manufactured from a gas and liquid impermeable heat sealable material and each having one end thereof pinched and sealed and one end open. Disposed within the applicator 41 is a stylus-shaped absorbent swab 46. As is best shown in the packaged, ready-to-activate applicator configuration of FIG. 9, the absorbent swab 46 projects outwardly from the open end of the proximal body 42, and the swab 46 is moved through the open end of distal cap 44 so that the proximal body 42 and distal cap 44 can be press fit together to establish an airtight seal at the interface therearound with the distal cap 44 surrounding the swab 46 projecting from proximal body 42.

In accordance with the present modification, and unlike the applicator 1 of FIGS. 1–3, the absorbent swab 46 has a hollow compartment 47 extending longitudinally therethrough. What is more, the medication wafer 8 of applicator 1 is replaced by an elongated medication plug 48. The medication plug 48, which, in the packaged, ready-to-activate applicator configuration of FIG. 9, is sized and shaped to fit snugly within the hollow compartment 47 of swab 46, is, as described above, a dehydrated topical astringent disinfectant for treating acne that has been reduced to crystalline form by lyophilization. Located proximally of the swab 46, with the medication plug 48 located in the compartment 47 thereof, is a deformable elastomeric septum 50. Like the applicator 1, a diluent 52 (best shown in FIG. 9) is stored in the proximal body 42 and ready to be introduced to the dehydrated astringent disinfectant of medication plug 48 to rehydrate and activate the acne medication. The septum 50 is located so as to extend laterally across the proximal body 42 to function as a barrier and thereby prevent the premature introduction of the diluent 52 to the medication plug 48 within absorbent swab 46.

The application and use of the stylus applicator 41 to apply a topical acne medication to a target site is identical to the application and use of the stylus applicator 1 which has been described when referring to FIG. 3A. Briefly, however, the user pulls the distal cap 44 off and away from the proximal body 42 to expose the absorbent swab 46 projecting from the proximal body 42. Then, the user compresses the proximal body 42 to cause the septum 50 to be displaced from its packaged alignment across the proximal body. Therefore, the liquid diluent 52 stored in the proximal body 42 will saturate the absorbent swab 46 and be introduced to the medication plug 48 therewithin. Accordingly, the solid astringent disinfectant of plug 48 is now mixed with the diluent and rehydrated to form a liquid acne medication 54. Finally, the user moves the stylus-shaped saturated swab 46 into contact with the acne to be treated to cause the acne medication 54 to be dispensed directly to the target site. When the topical treatment has been completed, the spent applicator is simply discarded.

It will be apparent that while the preferred embodiments of the invention have been shown and described, various modifications and changes may be made without departing from the true spirit and scope of the invention. For example, while the reconstituted medication has been disclosed herein as being adapted to treat acne, this should not be considered as a limitation of the invention. In this regard, it is to be understood that the topical astringent disinfectant to be applied to the tissue of the user may be used to treat skin disorders, other than acne.

Having thus set forth the preferred embodiments, what is claimed is:

We claim:

1. An applicator for applying a multi-constituent liquid medication to a tissue area in need of treatment, said applicator comprising:

a hollow, flexible body having an open distal end and a closed proximal end;

an absorbent swab retained within and projecting outwardly from the distal end of said body, said absorbent swab having a hollow compartment formed therewithin;

a dry medication stored within the hollow compartment of said absorbent swab;

a liquid stored within the proximal end of said body; and a defeatable fluid barrier located within said body between said distal and proximal ends to block the introduction of the liquid at the proximal end of said body to the dry medication within the hollow compartment of said absorbent swab at said distal end, the proximal end of said body being responsive to a compressive force applied thereto to generate a corresponding hydraulic pressure within the said liquid to defeat the fluid blocking integrity of said barrier so that said liquid can be introduced to and mixed with said dry medication with said hollow compartment to produce a liquid multi-constituent medication, said liquid medication being absorbed by said swab for application to the tissue area in need of treatment.

2. The applicator recited in claim 1, wherein said dry medication is a dehydrated astringent disinfectant that is rehydrated when said liquid is introduced thereto so as to produce said multi-constituent medication.

3. The applicator recited in claim 2, wherein said dehydrated astringent disinfectant is a crystalline wafer.

4. The applicator recited in claim 1, wherein said absorbent swab is an elongated stylus, one end of said stylus being received inwardly of the distal end of said applicator body to absorb the liquid multi-constituent medication, and the opposite end of said stylus projecting outwardly from said distal end to contact the tissue area to be treated.

5. The applicator recited in claim 1, wherein said defeatable fluid barrier is a deformable elastomeric septum extending in lateral alignment across the applicator body to form a fluid seal between the distal and proximal ends of said body, said elastomeric septum being responsive to the hydraulic pressure generated within said liquid for causing said septum to move out of said lateral alignment across said applicator body to thereby permit fluid communication between said proximal and distal ends so that the liquid at said proximal end can be introduced to and mixed with the dry medication at said distal end.

6. The applicator recited in claim 1, further comprising an end cap removably attached to the distal end of said applicator body to cover said absorbent swab projecting outwardly therefrom.

7. An applicator for applying a multi-constituent liquid medication to a tissue area in need of treatment, said applicator comprising:

a hollow, flexible body having closed distal and proximal ends;

an absorbent swab retained entirely within said body at the distal end thereof;

a dry medication stored within said body and communicating with said absorbent swab;

a liquid stored within said body at the proximal end thereof;

a defeatable fluid barrier located within said body between said distal and proximal ends to block the introduction of the liquid at the proximal end of said body to the dry medication at said distal end, the proximal end of said body being responsive to a compressive force applied thereto to generate a corresponding hydraulic pressure within said liquid to defeat the fluid blocking integrity of said barrier so that said liquid can be introduced to and mixed with said dry medication to produce a liquid multi-constituent medication, said liquid medication being absorbed by said swab; and a peripheral tearline formed in the distal end of said body surrounding said absorbent swab so that the distal end of said body can be separated from said proximal end to thereby expose said swab within said body so that said swab can be moved into contact with the tissue area in need of treatment and apply the multi-constituent medication thereto.

8. The applicator recited in claim 7, wherein said dry medication is a dehydrated astringent disinfectant that is rehydrated when said liquid is introduced thereto to produce said multi-constituent medication.

9. The applicator recited in claim 7, wherein said defeatable fluid barrier extends in lateral alignment across the applicator body to form a fluid seal between the distal and proximal ends, said barrier provided with at least one normally closed score line and being responsive to the hydraulic pressure generated within said liquid for causing said score line to open and thereby permit fluid communication between said proximal and distal ends of said applicator body so that the liquid at said proximal end can be introduced to and mixed with the dry medication at said distal end.

10. The applicator recited in claim 7, wherein said defeatable fluid barrier extends in lateral alignment across the applicator body to form a fluid seal between the distal and proximal ends thereof, said fluid barrier being displaced through said body and moved out of said lateral alignment across said body to open said fluid seal in response to the compressive force applied to the proximal end of said body.

11. An applicator for applying a multi-constituent liquid medication to a tissue area in need of treatment, said applicator comprising:

a hollow, flexible body having an open distal end and a closed proximal end;

an elongated stylus absorbent swab having a first end retained within the open distal end of said body and an opposite end projecting outwardly from said distal end to contact the tissue area to be treated;

a dry medication stored within the distal end of said body and communicating with said absorbent swab;

a liquid stored within the proximal end of said body;

a fluid barrier extending in lateral alignment across said body between said distal and proximal ends thereof to block the introduction of the liquid at the proximal end of said body to the dry medication at said distal end, the proximal end of said body being responsive to a compressive force applied thereto to generate a corresponding hydraulic pressure within the said liquid to displace said fluid barrier through said body and move said fluid barrier out of said lateral alignment across said body so that said liquid can be introduced to and mixed with said dry medication to produce a liquid multi-constituent medication, said liquid medication being absorbed by said swab for application to the tissue area in need of treatment; and an end cap removably attached to the distal end of said body to surround the opposite end of said absorbent swab projecting outwardly therefrom.

* * * * *